(12) United States Patent
Chen et al.

(10) Patent No.: US 8,285,355 B2
(45) Date of Patent: Oct. 9, 2012

(54) BIOMEDICAL ELECTRIC WAVE SENSOR

(75) Inventors: Yu-Han Chen, Hsinchu (TW); Paul C.-P. Chao, Hsinchu (TW); Lun-De Liao, Hsinchu (TW); Chin-Teng Lin, Hsinchu (TW); Jian-Ting Chen, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 271 days.

(21) Appl. No.: 12/778,508

(22) Filed: May 12, 2010

(65) Prior Publication Data

US 2011/0152659 A1   Jun. 23, 2011

(30) Foreign Application Priority Data

Dec. 18, 2009   (TW) ................... 98143587 A

(51) Int. Cl.
*A61B 5/04* (2006.01)
(52) U.S. Cl. ......... 600/383; 600/388; 600/393; 600/544
(58) Field of Classification Search .................. 600/372, 600/382–384, 386, 393, 544–545; 607/139–140
See application file for complete search history.

(56) References Cited

U.S. PATENT DOCUMENTS

| | | | |
|---|---|---|---|
| 5,038,782 A * | 8/1991 | Gevins et al. | 600/383 |
| 6,201,982 B1 * | 3/2001 | Menkes et al. | 600/386 |
| 2007/0225585 A1 * | 9/2007 | Washbon et al. | 600/393 |
| 2009/0030298 A1 * | 1/2009 | Matthews et al. | 600/372 |

FOREIGN PATENT DOCUMENTS

DE   3025955   * 7/1980

* cited by examiner

*Primary Examiner* — Linda Dvorak
*Assistant Examiner* — Brian M Antiskay
(74) *Attorney, Agent, or Firm* — Muncy, Geissler, Olds & Lowe, PLLC

(57) ABSTRACT

A biomedical electric wave sensor includes a base, a central pole, a dry electrode, a case, and a plurality of ribs. When the central pole lowers down, the ribs radiate and expand outward to push aside the hair of a subject, and the dry electrode exposes from the case and contacts the skin of the subject to measure a physiological electric wave signal from the subject. The present invention may overcome the intervention problem caused by hair and achieve the measurement of biomedical electric wave signal.

15 Claims, 5 Drawing Sheets

BIOMEDICAL ELECTRIC WAVE SENSOR

BACKGROUND OF THE INVENTION

1. Field of the Invention

The present invention relates to a biomedical electric wave sensor, particularly to a biomedical electric wave sensor capable of pushing aside hair.

2. Description of the Prior Art

The electric wave signal measurement has been widely applied in many fields such as military, biomedicine and man-machine systems and is used in biomedicine field for measuring EEG (electroencephalography), ECG (electrocardiography), EMG (electromyography) and so on.

Conventional electric wave signal measuring instruments usually adopt wet electrodes, which require conducting gel for proper functioning. However, the conducting gel may cause illness of patients, e.g. allergy or swelling, and can not be long-acting since the conductivity thereof would decrease with time.

Dry electrodes have been recently developed to resolve the aforementioned problems of wet electrodes. Most of the available dry electrodes are made by microstructure process, e.g. MEMS (Micro Electro Mechanical Systems), or CNTs (carbon nanotubes) and used in the form of penetrating the epidermis when in contact of the skin for achieving better conductivity and measurement.

As mentioned, the dry electrodes need to be in contact with the skin to actuate; however, the dry microstructure electrodes have short length (about 0.1 mm to 0.2 mm) and hair may cause intervention problems when used in practice. For example, the dry microstructure electrodes may be blocked by hair when applied for multiple point EEG measurement. Cutting the hair in advance is the main measure taken for now to overcome the intervention problem caused by hair; however, it is neither convenient nor applicable in many situations.

Besides, one of the development goals for EEG systems is being used as a portable device for common applications in addition to medicine field, e.g. a monitor system for monitoring long time drivers, or a computer system controlled by human brain. Thus, it is obviously not desirable to cut the hair when using these portable devices with EEG systems.

To sum up, it is now a current goal to develop a novel biomedical electric wave sensor which overcomes the intervention problem caused by hair.

SUMMARY OF THE INVENTION

The present invention is directed to providing a biomedical electric wave sensor that may overcome the intervention problem caused by hair and achieve the measurement of biomedical electric wave signal.

According to one embodiment of the present invention, a biomedical electric wave sensor includes a base, a central pole, a case, a plurality of ribs and a top disk. The base includes a plurality of holes at a rim of the base and lower surface of the base is configured as a dry electrode. The case houses the base and exposes the lower surface of the base. The central pole is connected to an upper surface of the base, penetrates through the case and is configured for lifting and lowering relative to the case. The ribs are configured at an inner side of the case corresponding to the holes, radiate inward relative to the central pole, penetrate through the holes and protrude from the lower surface of the base. As the central pole lowers down, the ribs protruding from the lower surface of the base radiate and expand outward to push aside the hair of a subject, and the dry electrode is exposed from the case and contacts the skin of the subject to measure a physiological electric wave signal from the subject.

Other advantages of the present invention will become apparent from the following descriptions taken in conjunction with the accompanying drawings wherein are set forth, by way of illustration and example, certain embodiments of the present invention.

DESCRIPTION OF THE PREFERRED EMBODIMENT

Figure 1:
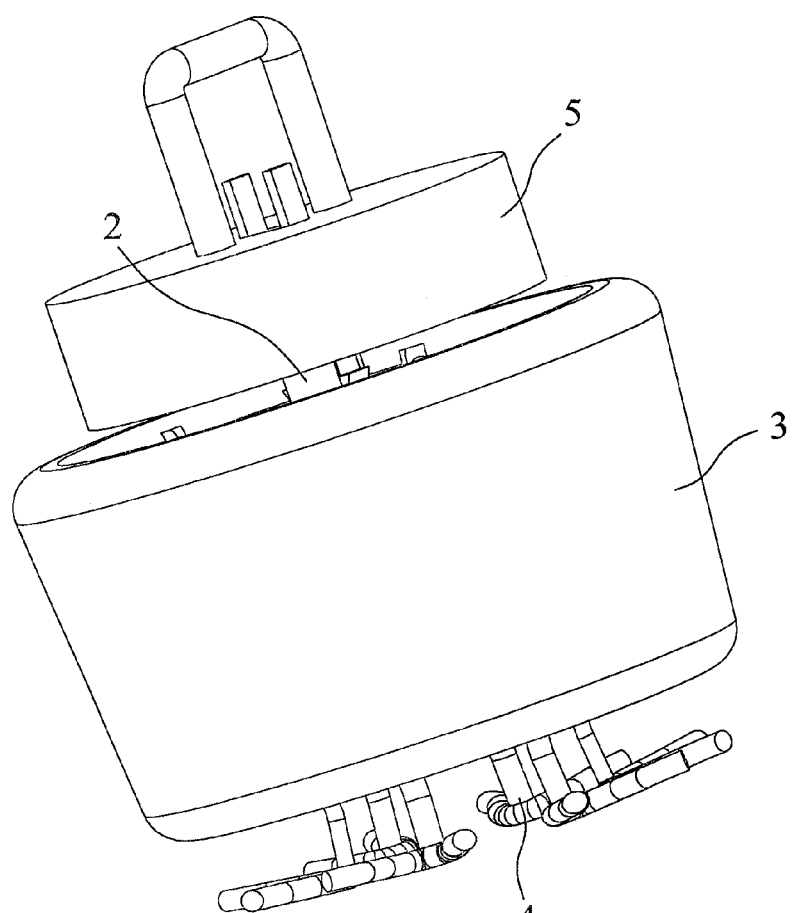
FIG. 1 is a side view illustrating an external feature of a biomedical electric wave sensor according to one embodiment of the present invention.
Figure 2:
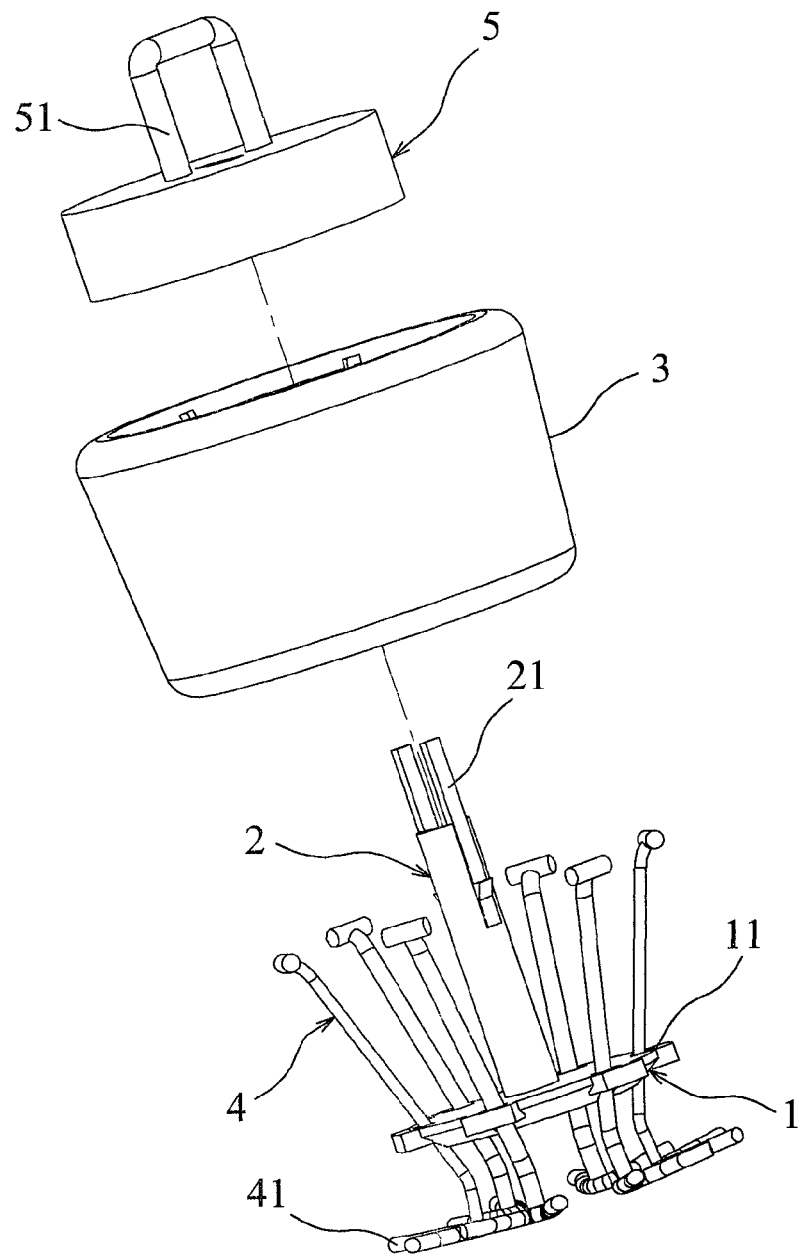
FIG. 2 is an exploded view illustrating components of the biomedical electric wave sensor according to one embodiment of the present invention.

Refer to FIGS. 1 and 2, respectively illustrating the external feature and exploded view of a biomedical electric wave sensor according to one embodiment of the present invention. The main body of the biomedical electric wave sensor includes a base 1, a central pole 2, a case 3, a plurality of ribs 4 and a top disk 5. The base 1 includes a plurality of holes 11 at a rim of the base 1. The case 3 houses the base 1 and exposes the lower surface of the base 3. The case 3 and the base 1 are set correspondingly; preferably, the base 1 and the case 3 have a round shape, e.g., the base 1 may be a round disk, and the case 3 may be a round tube; or the base 1 and the case 3 have a regular polygon shape.

Here, the central pole 2 is connected to the upper surface of the base 1. In one embodiment, the central pole 2 and the base 1 may be formed integrally, and the central pole 2 penetrates through a round disk (not illustrated) in the case 3 and is configured for lifting and lowering relative to the case 3. The lower surface of the base 1 is configured as a dry electrode 12. The dry electrode may include a plurality of microstructure probes, e.g. MEMS (Micro Electro Mechanical Systems) probes or CNT (carbon nanotubes) probes.

The ribs 4 are configured at the inner side of the case 3, wherein one end of the ribs 4 begin from an upper and peripheral portion in the case 3; the bodies of the ribs radiates inward and downward relative to the central pole 2, penetrates through the holes 11 and protrudes from the lower surface of the base 1; the other ends of the ribs 4 are thus more towards the central pole 2 and exposed outside the case 3. The ribs 4 may include a hair-dividing mechanism 41 extending from a bottom of each rib 4. The hair-dividing mechanism 41 expands outward, and preferably has a V shape or a rake shape for separating the hair apart when pushed.

In addition, the pushing mechanism of the present invention may be controlled with a top disk 5. The top disk 5, preferably having a round shape, may have its bottom connected to a tenon 21 of the central pole 2. The tenon 21, preferably made of plastic material, may be configured for the central pole 2 to set against the round disk 31 (not illustrated in FIGS. 1 and 2) as the central pole 2 lowers down so as to keep ribs 4 expanded. A grip 51 may be configured at the top of the top disk 5 and used for actuating in conjunction with the tenon 21 to control the lifting or lowering of the central pole 2 resulted in the expanding and closing of the ribs 4 that protrude from the base 1.

Figure 3:
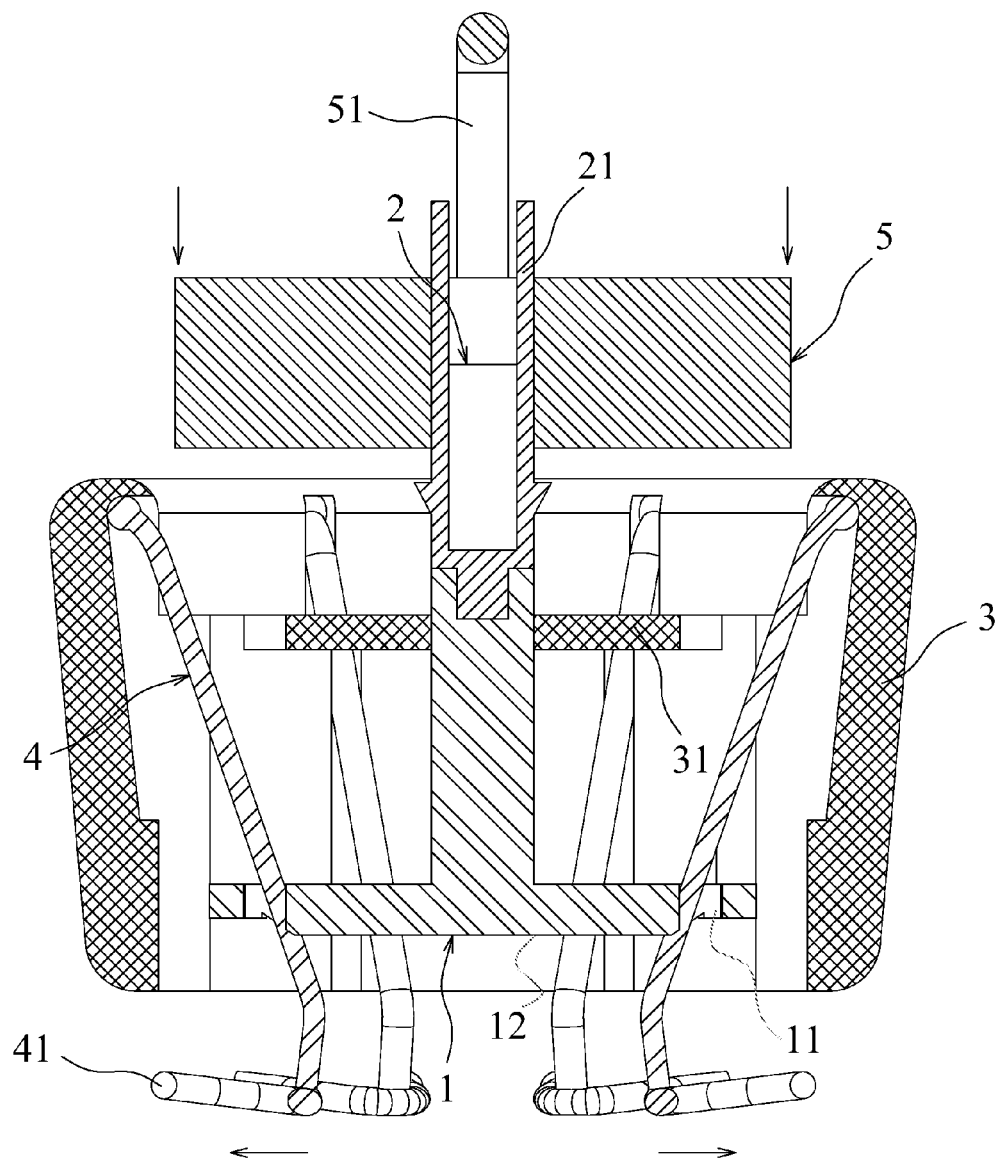
FIG. 3 is a sectional view illustrating the biomedical electric wave sensor in an unused status according to one embodiment of the present invention.

Description for pushing aside the hair and measuring the biomedical electric wave according to the present invention is now detailed. Refer to FIG. 3, which is a sectional view illustrating the biomedical electric wave sensor in an unused status according to one embodiment of the present invention. As illustrated, an umbrella structure is formed with the base 1, the central pole 2, the ribs 4 and the top disk 5. In this embodiment, the base 1 is a little bit smaller that the inner side of the case 3 in size. The ribs 4 are set corresponding to the holes 11, and one end of each rib 4 is fixed to the inner side of the case 3; therefore, the other end of each rib 4 radiates inward relative to the central pole 2. Next refer to FIG. 4, which is a sectional view illustrating the biomedical electric wave sensor in use according to one embodiment of the present invention. When the top disk 5 is pushed with an external force, the central pole 2 connected with the base 1 lowers down, and the end of each rib 4 that is not fixed to the case 3 and penetrates the hole 11 is propelled by the base 1 and then radiates and expands outward to push aside the hair of a subject. The dry electrode 12 is then exposed from the case 3 and contacts the skin of the subject to measure a physiological electric wave signal from the subject. Thus, the length problem for conventional dry electrodes is overcome. The physiological electric wave signal detected by the dry electrode 12 may be transmitted though an internal circuit (not illustrated) in the central pole 2 for outputting.

Figure 4:
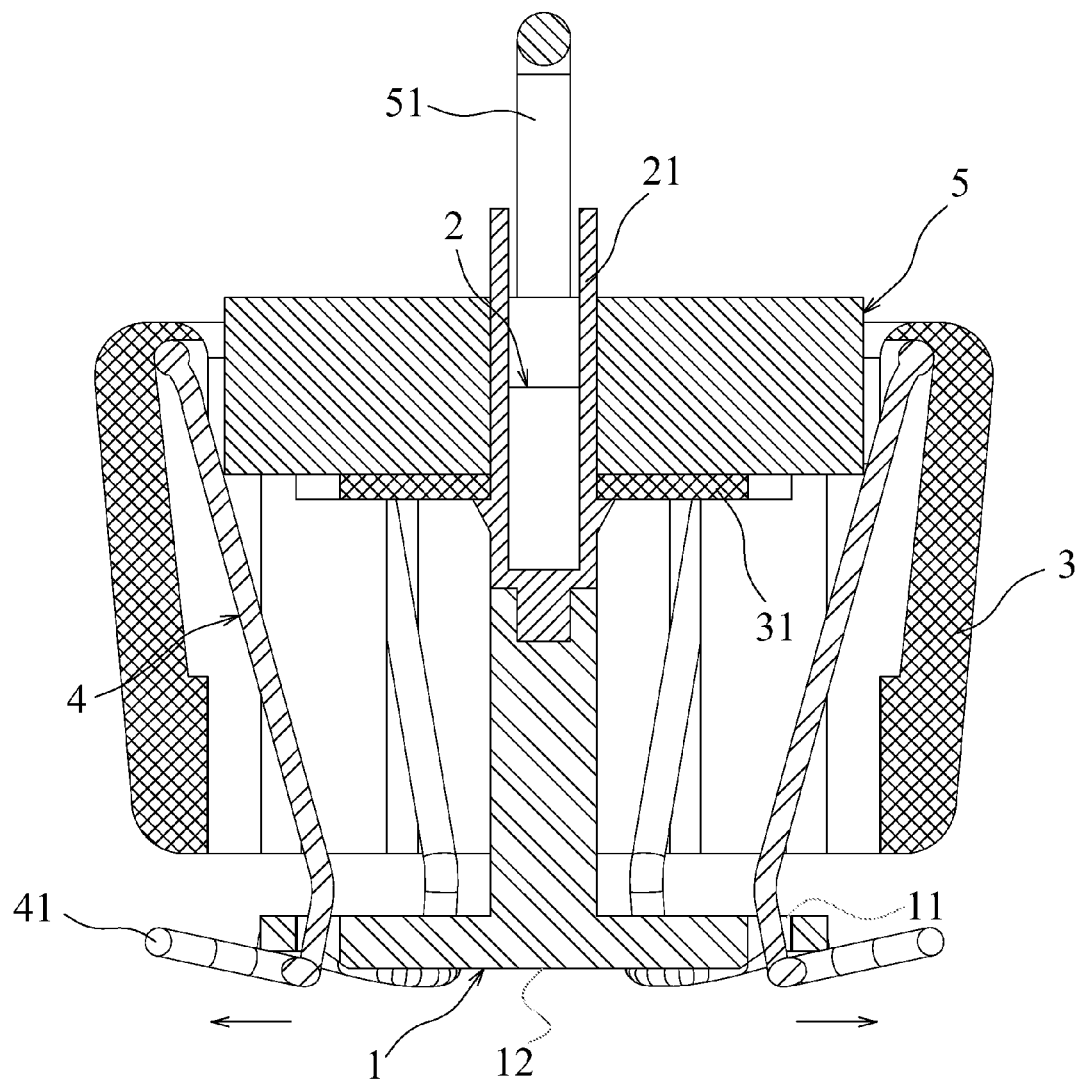
FIG. 4 is a sectional view illustrating the biomedical electric wave sensor in use according to one embodiment of the present invention.

Still referring to FIG. 4, in order to keep the ribs 4 and hair-dividing mechanism 41 of the present invention in an outward radiating and expanding status, an external force is applied to push the grip 51 of the top disk 5 toward the bottom of the biomedical electric wave sensor. The tenon 21 connected with the top disk 5 is lowered down to set against the lower surface of the round disk 31 of the case 3 and to lock the base 1 and central pole 2. The ribs are then retained in open status instead of being ejected, and the dry electrode 12 is kept exposed for pushing aside hair and measuring electric wave signal.

In case of loosening and folding the biomedical electric wave sensor of the present invention, the tenon 21 may be pressed or unscrewed to be loosened from bearing against the lower surface of the round disk 31, and the central pole 2 is then lifted by pulling the grip 51, through which the base 1 and the dry electrode 12 are retracted. The ribs 4 (particularly the portion protruding from the base 1) thus return to the initial state of inward radiating.

Figure 5:
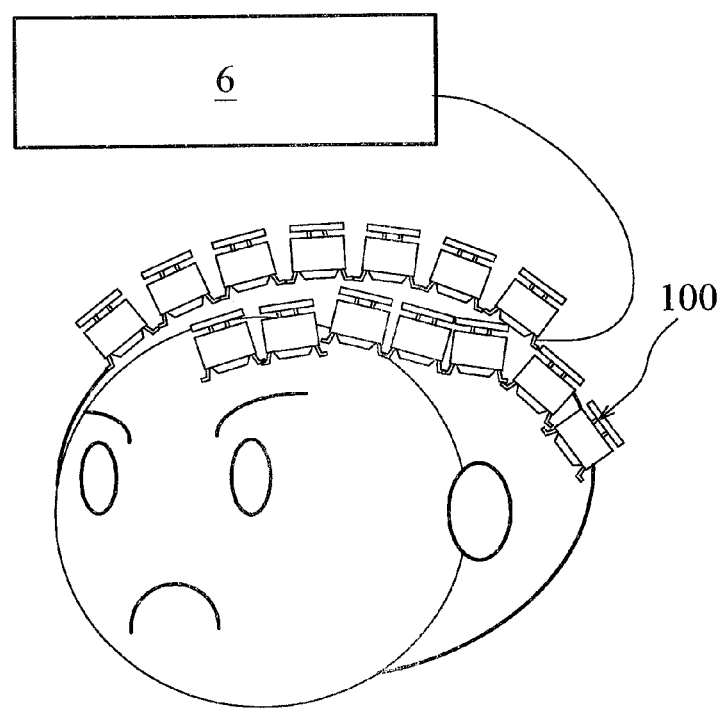
FIG. 5 is a schematic diagram illustrating the application of the biomedical electric wave sensor according to one embodiment of the present invention.

Refer to FIG. 5, which is a schematic diagram illustrating the application of the biomedical electric wave sensor according to one embodiment of the present invention. In this exemplary embodiment, the biomedical electric wave sensor 100 of the present invention is placed on the head of a subject for measuring the EEG signal. As illustrated, multiple biomedical electric wave sensors of the present invention may be mounted in array with each biomedical electric wave sensor placed at each measuring point for measuring physiological status in real-time. A back-end system 6 is then used for subsequent analysis and/or performing corresponding reaction.

As mentioned before, the present invention may be applied in EEG (electroencephalography), ECG (Electrocardiography), EMG (Electromyography), and so on.

To sum up, the biomedical electric wave sensor of the present invention may push aside the hair of the subject and expose the dry electrode from the case to contact the skin of the subject to measure a physiological electric wave signal from the subject. Therefore, the present invention may overcome the intervention problem caused by hair and be applied in portable devices with EEG systems.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A biomedical electric wave sensor, comprising:
    a base comprising a plurality of holes at a rim of the base, wherein a lower surface of the base is configured as a dry electrode;
    a case housing the base and exposing the lower surface of the base;
    a central pole connected to an upper surface of the base, penetrating through the case and configured for lifting and lowering relative to the case; and
    a plurality of ribs configured at an inner side of the case corresponding to the holes, the ribs radiating inward relative to the central pole, penetrating through the holes and protruding from the lower surface of the base, wherein as the central pole lowers down, the ribs protruding from the lower surface of the base radiate and expand outward to push aside hair of a subject, and the dry electrode is exposed from the case and contacts skin of the subject to measure a physiological electric wave signal from the subject.

2. The biomedical electric wave sensor as claimed in claim 1, wherein the base has a round shape.

3. The biomedical electric wave sensor as claimed in claim 2, wherein the case has a round shape.

4. The biomedical electric wave sensor as claimed in claim 1, wherein the base has a regular polygon shape.

5. The biomedical electric wave sensor as claimed in claim 4, wherein the case has a regular polygon shape.

6. The biomedical electric wave sensor as claimed in claim 1, wherein the central pole comprises an internal circuit configured therewithin and electrically connected to the dry electrode for outputting the physiological electric wave signal.

7. The biomedical electric wave sensor as claimed in claim 1, wherein the case further comprises a round disk, and the central pole penetrates through the round disk.

8. The biomedical electric wave sensor as claimed in claim 7, wherein the central pole further comprises a tenon configured for retaining the round disk as the central pole lowers down.

9. The biomedical electric wave sensor as claimed in claim 8, wherein the tenon is made of plastic material.

10. The biomedical electric wave sensor as claimed in claim 1, further comprising a top disk connected with the central pole.

11. The biomedical electric wave sensor as claimed in claim 10, wherein the top disk further comprises a grip configuration on a top surface of the top disk.

12. The biomedical electric wave sensor as claimed in claim 1, further comprising a hair dividing mechanism extending from a bottom of each of the ribs.

13. The biomedical electric wave sensor as claimed in claim 12, wherein the hair-dividing mechanism has a V shape or a rake shape.

14. The biomedical electric wave sensor as claimed in claim 1, wherein the dry electrode comprises a plurality of microstructure probes.

15. The biomedical electric wave sensor as claimed in claim 14, wherein the microstructure probe comprises a plurality of MEMS (Micro Electro Mechanical Systems) probes or a plurality of CNT (carbon nanotubes) probes.

* * * * *